United States Patent
Morris et al.

(10) Patent No.: US 9,848,825 B2
(45) Date of Patent: Dec. 26, 2017

(54) WEARABLE SENSING BAND

(71) Applicant: MICROSOFT TECHNOLOGY LICENSING, LLC, Redmond, WA (US)

(72) Inventors: Dan Morris, Bellevue, WA (US); T. Scott Saponas, Woodinville, WA (US); Nicolas Villar, Cambridge (GB); Shwetak Patel, Seattle, WA (US); Greg R. Smith, Bellevue, WA (US); Desney Tan, Kirkland, WA (US)

(73) Assignee: MICROSOFT TECHNOLOGY LICENSING, LLC, Redmond, WA (US)

( * ) Notice: Subject to any disclaimer, the term of this patent is extended or adjusted under 35 U.S.C. 154(b) by 526 days.

(21) Appl. No.: 14/500,029

(22) Filed: Sep. 29, 2014

(65) Prior Publication Data

US 2016/0089081 A1    Mar. 31, 2016

(51) Int. Cl.
*A61B 5/00* (2006.01)
*A61B 5/0408* (2006.01)
(Continued)

(52) U.S. Cl.
CPC ......... *A61B 5/6831* (2013.01); *A61B 5/0006* (2013.01); *A61B 5/0044* (2013.01);
(Continued)

(58) Field of Classification Search
CPC ..... A61B 5/6831; A61B 5/0006; A61B 5/004; A61B 5/0082; A61B 5/02125;
(Continued)

(56) References Cited

U.S. PATENT DOCUMENTS

| | | |
|---|---|---|
| 4,830,017 A | 5/1989 | Perry et al. |
| 4,893,631 A | 1/1990 | Wenzel et al. |

(Continued)

FOREIGN PATENT DOCUMENTS

| | | |
|---|---|---|
| EP | 1440655 A1 | 7/2004 |
| EP | 1970000 A2 | 9/2008 |

(Continued)

OTHER PUBLICATIONS

McCombie et al., "Adaptive blood pressure estimation from wearable PPG sensors using peripheral artery pulse wave velocity measurements and multi-channel blind identification of local arterial dynamics," Conf. Proc. IEEE Eng. Med. Biol. Soc., Aug.-Sep. 2006, vol. 1, pp. 3521-3524.

(Continued)

*Primary Examiner* — Scott Getzow
(74) *Attorney, Agent, or Firm* — Lyon & Harr LLP; Richard T. Lyon

(57) ABSTRACT

A wearable sensing band is presented that generally provides a non-intrusive way to measure a person's cardiovascular vital signs including pulse transit time and pulse wave velocity. The band includes a strap with one or more primary electrocardiography (ECG) electrodes which are in contact with a first portion of the user's body, one or more secondary ECG electrodes, and one or more pulse pressure wave arrival (PPWA) sensors. The primary and secondary ECG electrodes detect an ECG signal whenever the secondary ECG electrodes make electrical contact with the second portion of the user's body, and the PPWA sensors sense an arrival of a pulse pressure wave to the first portion of the user's body from the user's heart. The ECG signal and PPWA sensor(s) readings are used to compute at least one of a pulse transit time (PTT) or a pulse wave velocity (PWV) of the user.

12 Claims, 5 Drawing Sheets

(51) Int. Cl.

| | |
|---|---|
| *A61B 5/021* | (2006.01) |
| *A61B 5/04* | (2006.01) |
| *A61B 5/029* | (2006.01) |
| *A61B 5/026* | (2006.01) |
| *A61B 5/0265* | (2006.01) |
| *A61B 5/024* | (2006.01) |
| *A61B 5/0402* | (2006.01) |
| *A61B 5/02* | (2006.01) |
| *A61B 5/107* | (2006.01) |

(52) U.S. Cl.
CPC ............ *A61B 5/0082* (2013.01); *A61B 5/029* (2013.01); *A61B 5/0261* (2013.01); *A61B 5/0265* (2013.01); *A61B 5/02125* (2013.01); *A61B 5/02416* (2013.01); *A61B 5/0402* (2013.01); *A61B 5/04012* (2013.01); *A61B 5/04085* (2013.01); *A61B 5/681* (2013.01); *A61B 5/6823* (2013.01); *A61B 5/6824* (2013.01); *A61B 5/6828* (2013.01); *A61B 5/6829* (2013.01); *A61B 5/7246* (2013.01); *A61B 5/02007* (2013.01); *A61B 5/1079* (2013.01); *A61B 2562/0247* (2013.01); *A61B 2576/023* (2013.01)

(58) Field of Classification Search
CPC . A61B 5/02416; A61B 5/0261; A61B 5/0265; A61B 5/029; A61B 5/04012; A61B 5/0402; A61B 5/04085; A61B 5/681; A61B 5/6823; A61B 5/6824; A61B 5/6828; A61B 5/6829; A61B 5/7246
See application file for complete search history.

(56) References Cited

U.S. PATENT DOCUMENTS

| | | | |
|---|---|---|---|
| 4,987,898 | A | 1/1991 | Sones |
| 5,243,992 | A | 9/1993 | Eckerle et al. |
| 5,617,867 | A | 4/1997 | Butterfield et al. |
| 6,371,920 | B1 | 4/2002 | Kamimoto et al. |
| 6,443,906 | B1 | 9/2002 | Ting et al. |
| 6,475,153 | B1 | 11/2002 | Khair et al. |
| 6,723,054 | B1 | 4/2004 | Baruch et al. |
| 7,539,532 | B2 | 5/2009 | Tran |
| 2003/0176815 | A1 | 9/2003 | Baba |
| 2005/0228297 | A1 | 10/2005 | Banet et al. |
| 2006/0252999 | A1 | 11/2006 | Devaul et al. |
| 2007/0049461 | A1 | 3/2007 | Kim |
| 2007/0167844 | A1 | 7/2007 | Asada et al. |
| 2008/0039731 | A1 | 2/2008 | McCombie et al. |
| 2009/0216132 | A1 | 8/2009 | Orbach |
| 2010/0081951 | A1 | 4/2010 | Wong |
| 2010/0106029 | A1 | 4/2010 | Fraden |
| 2010/0292589 | A1 | 11/2010 | Goodman |
| 2011/0003665 | A1 | 1/2011 | Burton et al. |
| 2011/0152637 | A1 | 6/2011 | Kateraas et al. |
| 2012/0244995 | A1 | 9/2012 | Dibenedetto et al. |
| 2013/0296723 | A1 | 11/2013 | Cho et al. |
| 2013/0338460 | A1 | 12/2013 | He et al. |
| 2014/0073969 | A1 | 3/2014 | Zou et al. |
| 2014/0107493 | A1 | 4/2014 | Yuen et al. |
| 2014/0167973 | A1 | 6/2014 | Letchner et al. |
| 2014/0249398 | A1 | 9/2014 | Morris et al. |
| 2014/0257533 | A1 | 9/2014 | Morris et al. |
| 2014/0257534 | A1 | 9/2014 | Morris et al. |
| 2014/0257535 | A1 | 9/2014 | Morris et al. |
| 2014/0274159 | A1 | 9/2014 | Bernheim Brush et al. |
| 2014/0278139 | A1 | 9/2014 | Hong et al. |
| 2014/0354527 | A1 | 12/2014 | Chen |
| 2015/0374310 | A1 | 12/2015 | Lee |

FOREIGN PATENT DOCUMENTS

| | | |
|---|---|---|
| EP | 2191771 A1 | 6/2010 |
| WO | 2007053146 A1 | 5/2007 |
| WO | 2008007361 A2 | 1/2008 |
| WO | 2013068955 A1 | 5/2013 |
| WO | 2014022906 A1 | 3/2014 |

OTHER PUBLICATIONS

Peng, et al., "A Flexible Capacitive Pressure Sensor Array for Pulse Diagnosis," In IEEE International Frequency Control Symposium (FCS), May 19, 2014, 2 Pages.

Alam Medical, "Alam Medical", http://www.complior.com, retrieved Sep. 28, 2014, p. 1.

Atcor Medical Pty Limited, "SphygmoCor Technology", http://atcormedical.com/sphygmocor.html, retrieved Jul. 28, 2014, 1 page.

Finapres Medical Systems, "Finapres", http://www.finapres.com/, retrieved Sep. 28, 2014, p. 1.

Fitnesskeeper, Inc., "RunKeeper—GPS Track Run Walk", https://play.google.com/store/apps/details?id=com.fitnesskeeper.runkeeper.pro&hl=en, retrieved Aug. 28, 2014, pp. 6.

Goodwin, "Expectations for the Apple iWatch, your interface with the digital world", http://www.linkedin.com/today/post/article/20140624134124-6433797-introducing-the-apple-iwatch-your-interface-with-the-digital-world, Jun. 24, 2014, pp. 15.

Healthstats International, "BPro", http://www.healthstats.com/index3.php?page=product_bppro_intro, retrieved Jul. 28, 2014, pp. 2.

Jilek, et al., "A wrist cuff method for acquisition and analysis of radial artery waveforms used for blood pressure measuring", ElectroScope, Oct. 2007, vol. 1, No. 3, pp. 1-4.

Lara, et al., "Centinela: A human activity recognition system based on acceleration and vital sign data", Pervasive and Mobile Computing, Oct. 2012, pp. 717-729, vol. 8, Issue 5, Elsevier.

Lee, "Samsung smart watch will monitor vital signs", http://www.sfgate.com/technology/article/Samsung-smart-watch-will-monitor-vital-signs-5511554.php, May 28, 2014, pp. 8.

Millar Inc., "Clinical Blood Pressure Measurement", http://millar.com/clinical/products, retrieved Jul. 28, 2014, pp. 1-3.

Morris, et al., U.S. Appl. No. 61/927,796, "Chair that Senses Cardiovascular Risk Factors", Jan. 15, 2014.

Omron Healthcare Co Ltd., "Central BP Measurement HEM-9000AI", http://www.omronhealthcare.com.hk/en/product-hem9000ai.html, retrieved Sep. 28, 2014, pp. 1-2.

Poh, et al., "A Wearable Sensor for Unobtrusive, Long-Term Assessment of Electrodermal Activity", Institute of Electrical and Electronics Engineers (IEEE) Transactions on Biomedical Engineering, May 2010, pp. 1243-1252, vol. 57, No. 5, IEEE.

Rainmaker, "Hands on with Samsung's new waterproof S5, activity tracker and Gear watches—with built-in heart rate sensor", http://www.dcrainmaker.com/2014/02/waterproof-activity-watcheswith.html, Feb. 24, 2014, pp. 64.

Small Business Innovation Research/Small Business Technology Transfer, "Wearable Sensor for Continuous Noninvasive Monitoring of Pulse Pressure", http://www.sbir.gov/sbirsearch/detail/5375, retrieved Jul. 24, 2014, pp. 1-2.

SRI International, "Arterial Tonometry for Blood Pressure Measurement", http://www.sri.com/engage/products-solutions/arterial-tonometry, retrieved Sep. 28, 2014, p. 1.

Sun, et al., "Activity-aware Mental Stress Detection Using Physiological Sensors", Mobile Computing, Applications, and Services—Second International Institute for Computer Sciences, Social Informatics and Telecommunications Engineering (ICST) Conference (MobiCASE 2010), Oct. 25-28, 2010, pp. 1-20, Springer Berlin Heidelberg.

TensioMed Ltd., "TensioMed Arteriograph", http://www.tensiomed.com/en/parg.html, retrieved Jul. 28, 2014, pp. 1-4.

Trafton, Anne, "Wearable blood pressure sensor offers 24/7 continuous monitoring", In Proceedings of MIT Tech Talk, Apr. 8, 2009, 3 pages.

(56) References Cited

OTHER PUBLICATIONS

Vandrico Solutions Inc., "Mio Alpha", http://vandrico.com/device/mio-alpha, Aug. 31, 2014, pp. 3.
"International Search Report and Written Opinion Issued in PCT Application No. PCT/US2015/051960", dated Nov. 18, 2015, 17 Pages.

WEARABLE SENSING BAND

BACKGROUND

Heart disease is the leading cause of death in the United States, accounting for around six hundred thousand deaths per year (nearly 31% of reported deaths in the United States). High blood pressure (hypertension) is one of the most well-understood risk factors for heart disease. Hypertension is a risk factor for stroke, heart attack, heart failure, arterial aneurysm, and is the leading cause of renal failure. In the United States alone, it is estimated that hypertension incurs billions in direct, yearly healthcare costs, and nearly 1,000 deaths daily. Hypertension is a significant public health issue, and nothing would save more lives than getting blood pressure under control.

Unfortunately, hypertension has no visible warning signs or symptoms, and many people do not even realize they have it. This is particularly unfortunate because hypertension is treatable: lifestyle changes, specifically diet and exercise, are known to be effective in preventing the progression of hypertension. Moreover, numerous medications are available to treat hypertension. Therefore, the key to preventing many heart disease-related deaths may simply be awareness of the risk.

Despite this, blood pressure readings have not gained much attention in the consumer space. Hypertension is still typically identified through infrequent screening (e.g., at an annual exam, health fair, etc.) or when seeking healthcare for an unrelated medical issue.

SUMMARY

Wearable sensing implementations described herein are generally applicable to measuring cardiovascular vital signs including, but not limited to, pulse transit time and pulse wave velocity. The measured cardiovascular vital signs can then be used in a variety of ways, such as estimating blood pressure.

The wearable sensing implementations described herein are realized in a wearable sensing band. In one implementation, this band includes a strap which is attached to a first portion of the user's body. One or more primary electrocardiography (ECG) electrodes are disposed on the strap. Whenever the wearable sensing band is worn by the user, the primary ECG electrodes are in electrical contact with the first portion of the user's body. There is also one or more secondary ECG electrodes disposed on the strap. Whenever the wearable sensing band is worn by the user, the secondary ECG electrodes are electrically isolated from the first portion of the user's body and are positioned so as to be contacted by a second portion of the user's body located on the opposite side of the user's heart from the first portion. Further, there is one or more pulse pressure wave arrival (PPWA) sensors disposed on the strap. Whenever the wearable sensing band is worn by the user, the PPWA sensors are in proximity to or contacting the first portion of the user's body. In general, the primary and secondary ECG electrodes detect an ECG signal whenever the secondary ECG electrodes make electrical contact with the second portion of the user's body, and the PPWA sensors sense an arrival of a pulse pressure wave to the first portion of the user's body from the user's heart. The ECG signal and PPWA sensor(s) readings are used in one implementation to compute at least one of a pulse transit time (PTT) or a pulse wave velocity (PWV) of the user.

It should be noted that the foregoing Summary is provided to introduce a selection of concepts, in a simplified form, that are further described below in the Detailed Description. This Summary is not intended to identify key features or essential features of the claimed subject matter, nor is it intended to be used as an aid in determining the scope of the claimed subject matter. Its sole purpose is to present some concepts of the claimed subject matter in a simplified form as a prelude to the more detailed description that is presented below.

DESCRIPTION OF THE DRAWINGS

The specific features, aspects, and advantages of the disclosure will become better understood with regard to the following description, appended claims, and accompanying drawings where:

DETAILED DESCRIPTION

Figure 1:
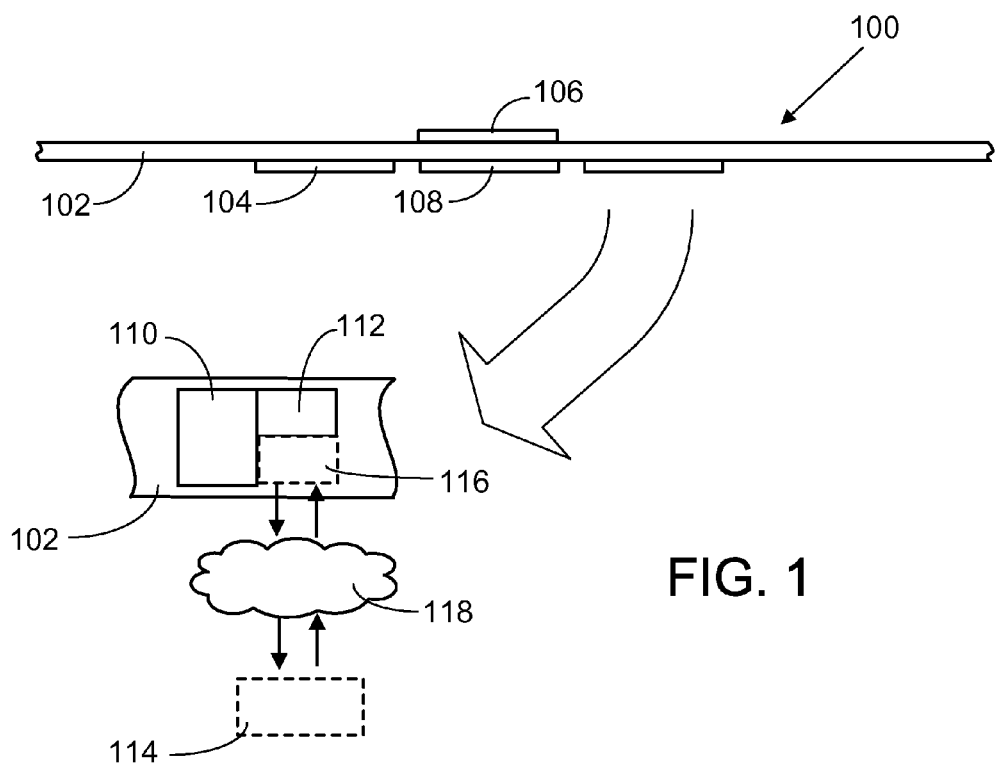
FIG. 1 is a simplified diagram of one exemplary implementation of a wearable sensing band.

In the following description of wearable sensing implementations reference is made to the accompanying drawings which form a part hereof, and in which are shown, by way of illustration, specific versions in which the wearable sensing implementations can be practiced. It is understood that other implementations can be utilized and structural changes can be made without departing from the scope thereof.

It is also noted that for the sake of clarity specific terminology will be resorted to in describing the wearable sensing implementations described herein and it is not intended for these implementations to be limited to the specific terms so chosen. Furthermore, it is to be understood that each specific term includes all its technical equivalents that operate in a broadly similar manner to achieve a similar purpose. Reference herein to "one implementation", or "another implementation", or an "exemplary implementation", or an "alternate implementation" means that a particular feature, a particular structure, or particular characteristics described in connection with the implementation can be included in at least one implementation of wearable sewnsing. The appearances of the phrases "in one implementation", "in another implementation", "in an exemplary implementation", and "in an alternate implementation" in various places in the specification are not necessarily all referring to the same implementation, nor are separate or alternative implementations mutually exclusive of other implementations. Yet furthermore, the order of process flow representing one or more implementations of wearable sensing does not inherently indicate any particular order or imply any limitations thereof.

As utilized herein, the terms "component," "system," "client" and the like are intended to refer to a computer-related entity, either hardware, software (e.g., in execution), firmware, or a combination thereof. For example, a component can be a process running on a processor, an object, an executable, a program, a function, a library, a subroutine, a computer, or a combination of software and hardware. By way of illustration, both an application running on a server and the server can be a component. One or more components can reside within a process and a component can be localized on one computer and/or distributed between two or more computers. The term "processor" is generally understood to refer to a hardware component, such as a processing unit of a computer system.

Furthermore, to the extent that the terms "includes," "including," "has," "contains," variants thereof, and other similar words are used in either this detailed description or the claims, these terms are intended to be inclusive in a manner similar to the term "comprising" as an open transition word without precluding any additional or other elements.

1.0 Wearable Sensing of Pulse Transit Time and Pulse Wave Velocity

Vital signs are indicators of the human body's most basic functions, and are useful in both detecting and monitoring medical conditions. The wearable sensing implementations described herein are generally applicable to measuring cardiovascular vital signs including, but not limited to, pulse transit time and pulse wave velocity. The measured cardiovascular vital signs can then be used in a variety of ways, such as estimating blood pressure.

Generally speaking, the term "pulse-transit time" is used herein to refer to the amount of time it takes for a pressure wave that is generated by blood being expelled from a user's heart (which is hereafter sometimes referred to as a pulse pressure wave) to travel through the user's arteries from one arterial site on the user's body to another arterial site on the user's body. More particularly and as will be appreciated from the more detailed description that follows, in one version of the wearable sensing implementations described herein where the cardiovascular vital signs of a user are measured using a wearable band that the user attaches to (e.g., wears on) a portion of their body, pulse-transit time refers to the amount of time it takes for the pulse pressure wave to travel from the user's heart, through their arteries, to the portion of the body upon which the wearable band is attached. As is appreciated in the arts of medicine and cardiovascular health, there is a known correlation between pulse-transit time and other cardiovascular metrics such as blood pressure, arterial compliance, and the hardening of artery walls. Although other body metrics (such as the user's height, weight and age, and the arterial distance between the just-described two arterial sites on the user's body, among other types of body metrics) influence the user's blood pressure, the pulse-transit time measurement that is made by the wearable sensing implementations can be used to determine the user's blood pressure based on the just-described known correlation between pulse-transit time and blood pressure.

Generally speaking, the term "pulse-wave velocity" is used herein to refer to the speed at which the just-described pulse pressure wave travels through a user's arteries from one arterial site on the user's body to another arterial site on the user's body. More particularly and as will be appreciated from the more detailed description that follows, in the just-described version of the wearable sensing implementations described herein where the cardiovascular vital signs of a user are measured using a wearable band that the user attaches to their body, pulse-wave velocity refers to the average speed at which the pulse pressure wave travels from the user's heart, through their arteries, to the portion of the body upon which the wearable band is attached. As is appreciated in the arts of medicine and cardiovascular health, there is a known correlation between pulse-wave velocity and cardiovascular diseases such as hypertension. More particularly, as a person ages their arteries generally get stiffer. This increasing arterial stiffness makes the person's heart work harder and also makes the pulse pressure wave travel faster through their arteries, thus increasing their risk of cardiovascular diseases such as hypertension.

As will be appreciated from the more detailed description that follows, the wearable sensing implementations described herein are advantageous for various reasons such as the following. The wearable sensing implementations provide users with a cost effective and easy to use assessment of their cardiovascular health. The wearable sensing implementations can also prevent many heart-disease-related deaths by making users who have hypertension aware of it. Once a given user is made aware of their having hypertension, the wearable sensing implementations can be used to routinely monitor the user's cardiovascular vital signs, and encourage the user to treat their hypertension by consulting with a doctor and making appropriate lifestyle changes. The wearable sensing implementations also measure users' cardiovascular vital signs in a non-invasive and non-intrusive (e.g., a passive) manner. The wearable sensing implementations thus allow users to routinely measure/monitor their cardiovascular vital signs without pain and discomfort.

As will also be appreciated from the more detailed description that follows, the wearable sensing implementations described herein can be employed in a variety of applications, and can also be realized in various types of computing devices. The wearable sensing implementations are also easy to operate, and are not restricted to being used by a trained medical technician or doctor in a controlled medical setting such as a laboratory or doctor's office. The wearable sensing implementations thus allow users to conveniently and automatically measure their cardiovascular vital signs at one or more opportunistic times during the normal course of their day while they are either stationary or ambulatory, including while they are involved in or performing a wide variety of physical activities.

1.1 Wearable Sensing Band

The wearable sensing implementations described herein generally provide a non-intrusive way to measure a person's pulse transit time and pulse wave velocity using a wearable sensing band. FIG. 1 illustrates one exemplary implementation of the wearable sensing band. The sensing band 100 includes one or more primary electrocardiography (ECG) electrodes 104 (one of which is shown) disposed on one side of a strap 102 such that whenever the sensing band is worn by a user, the primary ECG electrodes are in electrical contact with a first portion of the user's body. In one implementation, the strap 102 is configured (in any suitable way) to be wrapped around and tightened against a person's body. For example, the strap 102 can be configured to wrap around a person's wrist (like a watch), or forearm, or upper arm (like an armband commonly used to hold mobile phones or music players during exercise), or torso, or upper leg, or lower leg, or ankle, among other places. In general, any place on a person's body that a strap can be wrapped around and tightened, and which movement in an underlying artery can be sensed, would be a viable location. In another implementation, the strap is adhered to the person's body. In this case, any place on a person's body that a strap can be adhered to, and which movement in an underlying artery can be sensed, would be a viable location. The primary electrodes 104 are disposed on the side of the strap 102 that faces and touches the part of the person's body when the strap is worn. The term "primary" is employed only to indicate that these electrodes 104 touch the part of the person's body that the strap 102 is wrapped around or adhered to. The primary ECG electrodes 104 are of a rigid, metal type in one version; or of a flexible, conductive fabric type in another version. In addition, in one version, these electrodes 104 are mounted on the strap 102 in a visually obvious manner (as shown in FIG. 1), or in another version they are invisibly embedded into the strap. When multiple primary ECG electrodes 104 are employed, they can all be of the same type and mounting configuration, or any combination of the foregoing types and mounting configurations.

The wearable sensing band 100 also includes one or more secondary ECG electrodes 106 (one of which is shown) disposed on the strap 102 such that whenever the wearable sensing band is worn by the user, the secondary ECG electrodes are electrically isolated from the aforementioned first portion of the user's body. In addition, the secondary ECG electrodes 106 are positioned so as to be contacted by a second portion of the user's body located on the opposite side of the user's heart from the aforementioned first portion of the user's body. This contact with the second portion of the user's body is done whenever an ECG measurement is to be taken, as will be described in more detail later in this description. The secondary electrodes 106 are disposed on a surface of the strap 102 that does not touch the aforementioned first part of the person's body when the strap is worn. In one implementation, this is the side of the strap 102 opposite the side where the primary electrodes 104 are disposed (as shown in FIG. 1). It is noted that the term "secondary" is employed only to indicate that these electrodes 106 do not touch the part of the person's body that the strap 102 is wrapped around or adhered to. As with the primary ECG electrodes, the secondary ECG electrodes 106 are of a rigid, metal type in one version; or of a flexible, conductive fabric type in another version. In yet another version, the secondary ECG electrodes are of a type that can establish electrical contact with a person's body through that person's clothes. In addition, in one version, these electrodes 106 are mounted on the strap 102 in a visually obvious manner (as shown in FIG. 1), or in another version they are invisibly embedded into the strap. When multiple secondary ECG electrodes 106 are employed, they can all be of the same type and mounting configuration, or any combination of the foregoing types and mounting configurations.

It is noted that when multiple electrodes are employed for the primary ECG electrodes or secondary ECG electrodes, they can be configured in different ways. In one version, the multiple electrodes associated with an ECG electrode set (either primary or secondary or both) are electrically connected. This scenario is useful in assuring at least one of the electrodes in a set is making electrical contact with the user's body. In another version, the multiple electrodes associated with an ECG electrode set (either primary or secondary or both) are electrically isolated. In this scenario, the output from the electrically isolated electrode exhibiting the best signal can be chosen. In yet another version, the multiple electrodes associated with an ECG electrode set (either primary or secondary—but not both) includes a grounded electrode. This is useful as some ECG signal processing schemes employ a grounded electrode configuration.

The wearable sensing band 100 further includes one or more pulse pressure wave arrival (PPWA) sensors 108 (one of which is shown) disposed on the strap 102 such that whenever the wearable sensing band is worn by the user, the PPWA sensors are in proximity to or contacting the aforementioned first portion of the user's body. The PPWA sensors 108 are disposed on the side of the strap 102 that faces and touches the part of the person's body when the strap is worn. In the case where one or more of the sensors 108 do not contact the person's body, these sensors are embedded into the strap 102 but still facing the first part of the person's body when the band is worn.

In one implementation, the PPWA sensors are of the optical type with one or more illumination sources and one or more photosensors. The optical type sensors detect the change in shape of an artery as evidenced by movement of a person's skin overlying the artery when a pulse pressure wave passes through. In another implementation, the PPWA sensors are of the mechanical type, such as, but without limitation, piezoresistive pressure sensors that sense the motion of an underlying artery when the pulse arrives. When multiple PPWA sensors are employed, they can all be optical, all mechanical, or any combination of the two.

In operation, the primary 104 and secondary 106 ECG electrodes are used to detect an ECG signal when the secondary ECG electrodes make electrical contact with the aforementioned second portion of the user's body. As will be described shortly, the ECG signal is employed to identify a time when a pulse pressure wave leaves a person's heart. As for the PPWA sensors, they are used to sense a time of arrival of the pulse pressure wave at the aforementioned first portion of the user's body from the user's heart. Together, these two measurements are used to compute a pulse transit time as will be described in a section to follow.

1.1.1 Wrist-Bands

As indicated previously, the wearable sensing implementations described herein include versions that are worn on the wrist. These wrist-band versions provide an opportunity to include additional advantageous features and configurations. For example, in one version, the wrist-band takes the form of a wrist watch, and in another the wrist-band takes the form of a so-called "smart watch" with all its attendant computing, display and communication capabilities. It is noted that given the user interface capabilities of a smart watch, the wearable sensing implementations described herein employing this form can be configured via conventional means to display information to the wearer. For example, instructions for touching the previously-described secondary ECG electrodes with the second portion of the wearer's body on the opposite side of the heart from the banded wrist to initiate an ECG measurement could be displayed. In addition, results of the measurements could be displayed to the wearer.

While the primary and secondary ECG electrodes and PPWA sensors can be disposed anywhere on the strap, the watch-based versions of the wrist-band also provide an opportunity to make them part of the "watch" component (which is considered part of the strap for purposes of this description). For example, the primary ECG electrode(s) and/or PPWA sensors can be disposed on the back of the watch body. Additionally, the secondary ECG electrode(s) can be disposed on the face of the watch body.

Figure 2:
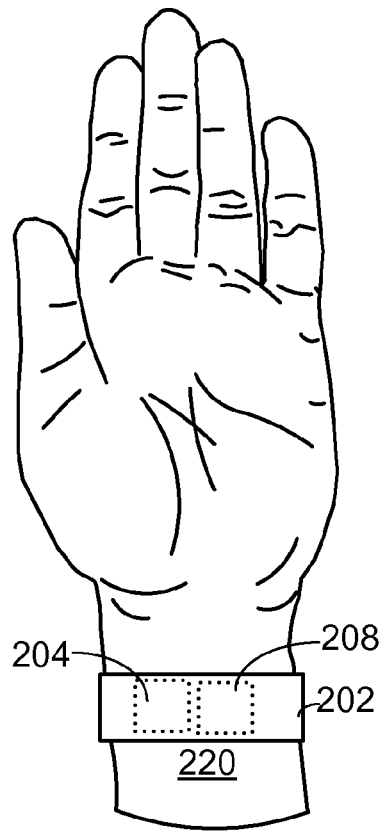
FIG. 2 is a simplified diagram a version of the wearable sensing band of FIG. 1 shown on the wrist of a person with a pulse pressure wave arrival (PPWA) sensor and a primary electrocardiography (ECG) electrode disposed on a part of the strap that touches the underside (i.e., palm side) of the person's wrist.

It is further noted that given the proximity of the underside (i.e., palm side) of the wrist to arteries (such as the radial artery), placement of the PPWA sensors 208 on the part of the strap 202 that touches this portion of the wrist 220 (as shown in FIG. 2) is advantageous for the reasons described previously. However, while the primary ECG electrode(s) 204 can be disposed anywhere on strap 202 of the wrist-band versions of the wearable sensing implementations described herein, it is believed that placement of these electrode(s) on the part of the strap that touches the underside of the wrist 220 is advantageous. In particular, placement of the primary ECG electrode(s) 204 on the part of the strap 202 that touches the underside of the wrist 220 can improve PTT and PWV sensing, especially in non-exercise conditions. It is noted that in FIG. 2, the primary ECG electrode(s) 204 and PPWA sensors 208 are shown as dotted line boxes to indicate they are on the inward facing side of the strap 202.

1.2 Pulse Transit Time Computation

As indicated previously, pulse transit time (PTT) is the time it takes a pressure wave generated by blood being expelled from the heart to travel between two arterial sites. Note that this is not the time it takes for any given molecule of blood to move the same distance. Rather it is the time it takes for a pressure wave to travel through the blood (which is very fast—on the order of 200-400 milliseconds from the heart to a person's wrist). In the context of the wearable sensing implementations described herein, PTT is the time it takes a pressure wave to travel from a person's heart to the aforementioned first portion of the user's body that the band is wrapped around (or adhered to) and which overlies an artery (e.g., the radial artery in a person's wrist). Advantageously, the PTT correlates with various body metrics, such as blood pressure, arterial compliance, and the hardening of artery walls.

As indicated previously, computing the PTT involves processing measurements from the ECG electrodes and the PPWA sensors. In general, the measured ECG signal is employed to identify the time when a pulse pressure wave leaves a person's heart using conventional methods (including noise reduction and motion compensation), and the PPWA sensors sense the time the pulse pressure wave arrives at the aforementioned first portion of the user's body. The PTT reading is then established by calculating the amount of time that passes between the pulse pressure wave leaving the heart, and arriving at the arterial site being measured (i.e., the aforementioned first portion of the user's body).

The measured ECG electrodes and PPWA sensors signals are processed and the PTT computation is accomplished using one or more computing devices (such as those described in the forthcoming exemplary operating environments section), and a computer program executing thereon. The aforementioned processing and computations will be described in more detail later in this description. Referring to FIG. 1 once again, in one implementation, the PWVS band 100 includes a computing device 110 that is employed for the foregoing processing and computations. In addition, the PWVS band 100 includes an appropriate conventional storage component 112 for storing any data needed to accomplish the aforementioned processing and computations, as well storing the results of the processing and computations.

Figure 3:
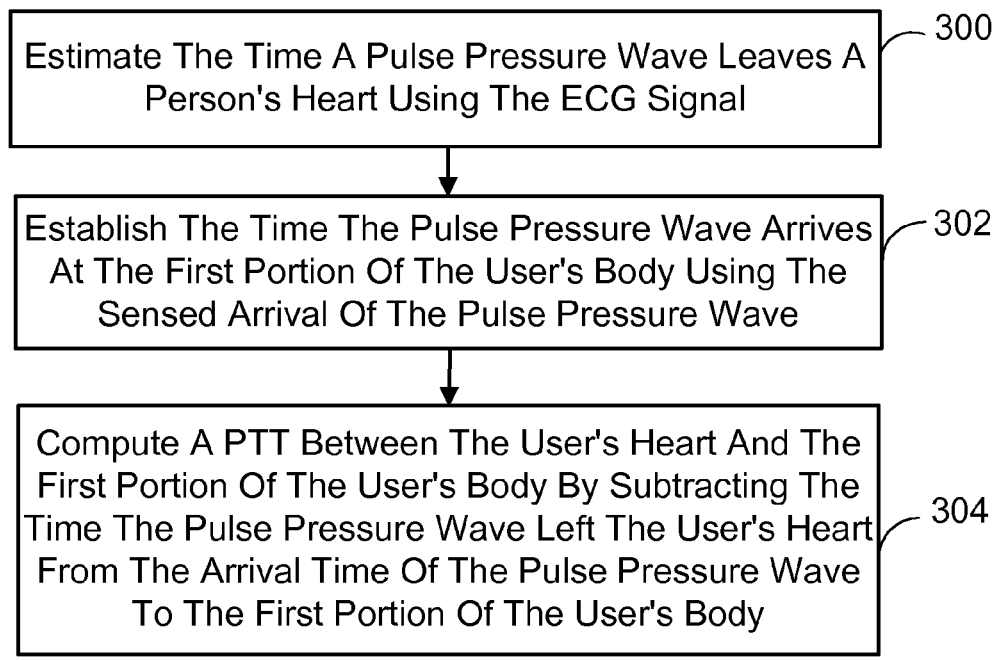
FIG. 3 is a flow diagram illustrating an exemplary embodiment, in simplified form, of a process for computing a pulse transit time (PTT) between a user's heart and a portion of the user's body underlying the wearable sensing band.

In view of the foregoing and referring now to FIG. 3, the computing device or devices are directed by the aforementioned computer program to, in one version, estimate the time a pulse pressure wave leaves a person's heart using an ECG signal (process action 300). The time this pulse pressure wave arrives at the aforementioned first portion of the user's body is then established using the sensed arrival of the pulse pressure wave (process action 302). A PTT between the user's heart and the first portion of the user's body is then computed by subtracting the time the pulse pressure wave left the user's heart from the arrival time of the pulse pressure wave to the first portion of the user's body (process action 304).

The foregoing process is initiated when the user causes an ECG signal to be generated. In one implementation, this involves the user touching the previously-described secondary ECG electrodes with or to the aforementioned second portion of the user's body. For example, in one version, the wearable sensing band is worn on a user's wrist. To initiate the generation and capture of the ECG signal, in one version, the user touches the secondary ECG electrodes with a finger or fingers (i.e., the second portion of the user's body) of the hand on the opposite side of the body from the banded wrist. In another version, the user reaches across his or her body with the banded wrist and touches the secondary ECG electrodes to a location (i.e., the second portion of the user's body) on the opposite side of the user's heart from the banded wrist. For example, the user might touch the secondary ECG electrodes of the sensing band worn on his or her right wrist to the left side of his or her torso. This alternate version has the advantage of allowing one-handed operation. This is particularly practical if the electrodes are able to work through clothing as described previously.

It is noted that in one version, the wearable sensing band is worn on a user's ankle or on the upper leg. The generation and capture of the ECG signal is initiated in much the same way as the foregoing exemplary versions with the user touching the secondary ECG electrodes to a second portion of the user's body (e.g., the opposite ankle or upper leg), or with a second portion of the user's body (e.g., the finger or fingers of the hand on the opposite side of the heart from the banded ankle or upper leg). While somewhat less convenient, the foregoing configuration would measure a pulse travel path that includes the descending aorta (the main artery that carries blood through the torso)—thus potentially providing an even more valuable risk assessment.

In alternate implementations, the measured ECG electrodes and PPWA sensors signals (or a representation thereof) are sent to a server or cloud service that is remote from the person wearing the wearable sensing band 100. It is noted that the term "cloud service" is used herein to refer to a web-based service that operates in the cloud and can be hosted on (e.g., deployed at) a plurality of computing centers that can be located in different geographic regions (e.g., different regions of the world) and can be concurrently used by a plurality of remote end users. In other words, a cloud service is a web-based service that is geographically distributed. In one implementation, the remote server or cloud service accomplishes the aforementioned processing and computations. Referring once again to FIG. 1, the server or cloud service 114 is shown using a dashed-line box to indicate it is an optional component. In the alternate implementations, the wearable sensing band 100 further includes an appropriate conventional communications component 116 for communicating with the remote server or cloud service 114. Any communication scheme can be employed. For example, via a computer network 118 (such as the Internet or a proprietary intranet), as shown in FIG. 1. The communications component 116 is shown as a dashed line box in FIG. 1 to indicate that it is also an optional component. It is noted that the computing device 110 and storage component 112 are retained in these alternate implementations to facilitate the transfer of the measured ECG electrodes and PPWA sensors signals (or a representation thereof) to the remote server or cloud service 114. Once the aforementioned processing and computations are completed the remote server or cloud service 114 can relay the results to substantially any other computing device, server or cloud service (e.g., a computing device of a doctor of the user, a computing device of a manager of the user, a health monitoring service, back to the wearable sensing band 100, and so on).

In yet other implementations, the aforementioned processing and computations are accomplished by the wearable sensing band 100, which includes the computing device 110, the storage component 112 and the communications component 116. In these implementations, when the processing and computations are completed the results are sent to another computing device, server or cloud service (e.g., a computing device of a doctor of the user, a computing device of a manager of the user, a health monitoring service, and so on).

1.3 Pulse Wave Velocity Computation

While a PTT measurement is useful and has some correlation to cardiovascular health, it does not tell the full picture. The distance the pressure wave travels between a person's heart and the aforementioned first portion of the body has significance. For example, as indicated previously, the speed at which a pulse pressure wave travels through an artery (or series of arteries) is indicative of arterial stiffness. In general, the faster the pulse pressure wave travels, the stiffer the artery (or arteries) the wave travels through tends to be. Stiffer arteries are generally counter-indicative of good cardiovascular health. Thus, two people could have the same measured PTT, but if the distance the pulse pressure wave traveled is significantly different for these two people, one could be in good cardiovascular health and the other not. For example, if the PTT is measured from the heart to the wrist of a tall person having stiffer arteries and a smaller person having more flexible arteries, because the arterial distance would be further in the taller person, these two individuals could have the same PTT even though the pulse pressure wave is traveling faster through the arteries of the taller person (thus indicating stiffer arteries and possible poorer cardiovascular health). Thus, a measurement of the speed of a pulse pressure wave could be more indicative of cardiovascular health than just the PTT.

Pulse wave velocity (PWV) is the speed at which a pulse pressure wave travels through an artery, either at one particular location or averaged over some distance. In the context of the wearable sensing implementations described herein, PWV refers to the average velocity of the pulse pressure wave as it travels from a person's heart to the aforementioned first portion of the user's body.

Figure 4:
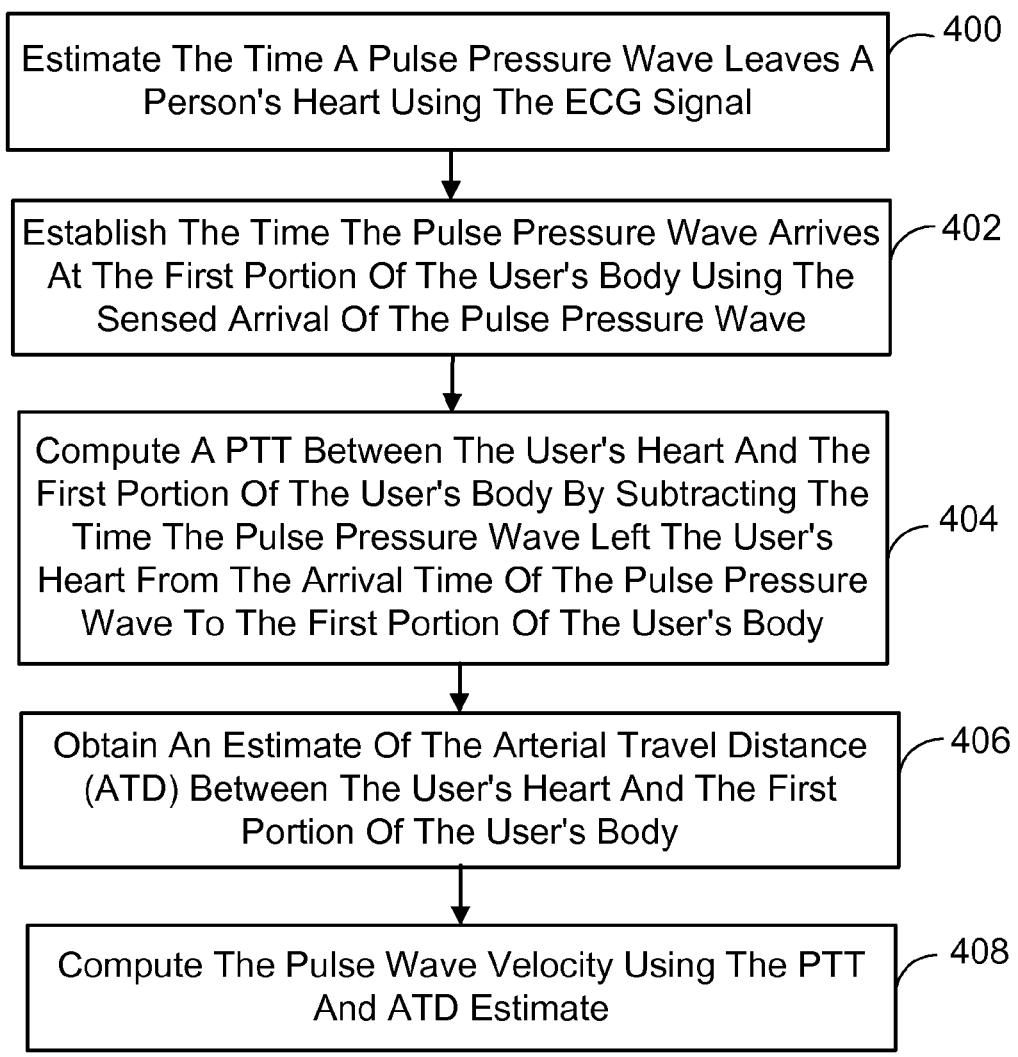
FIG. 4 is a flow diagram illustrating an exemplary embodiment, in simplified form, of a process for computing a pulse wave velocity (PWV) from a user's heart to a portion of the user's body underlying the wearable sensing band.

The measured ECG electrodes and PPWA sensors signals are processed and the PTT and PWV computations are accomplished using one or more computing devices and a computer program executing thereon (as described previously and employing the aforementioned computing device, storage component and communications component in the wearable sensing band, as needed). In view of this and referring now to FIG. 4, the computing device or devices are directed by the aforementioned program modules to, in one version, estimate the time a pulse pressure wave leaves a person's heart using an ECG signal (process action 400). The time this pulse pressure wave arrives at the aforementioned first portion of the user's body is then established using the sensed arrival of the pulse pressure wave (process action 402). A PTT between the user's heart and the first portion of the user's body is then computed by subtracting the time the pulse pressure wave left the user's heart from the arrival time of the pulse pressure wave to the first portion of the user's body (process action 404). Next, an estimate of the arterial travel distance (ATD) between the user's heart and the first portion of the user's body is obtained (process action 406). And finally, the pulse wave velocity is computed using the PTT and ATD estimate (process action 408).

1.3.1 Arterial Travel Distance Estimation

As indicated, in order to compute the PWV, an estimate of the travel distance between the heart and the aforementioned first portion of the user's body is needed. It can be measured directly, such as by a catheter inside the artery that measures how fast the pressure wave is propagating over the surface of the catheter. However, it's more commonly obtained by measuring the time taken for a pulse pressure wave to travel between two sites (i.e., PTT), measuring the distance between those sites, and dividing distance by time to get velocity. The distance from a person's heart to the aforementioned first portion to the person's body will depend on the location of that portion of the body. For example, if the wearable PWVS band is wrapped around a person's wrist, this distance includes a segment of the ascending aorta, the subclavian artery (near the shoulders), the brachial artery (in the upper arm), and some of the radial artery (in the wrist).

In research or clinical settings, the aforementioned distance (which will sometimes be referred to herein as the arterial travel distance (ATD)) is measured directly via x-ray or catheter insertion; or a technician will mark locations on the body that roughly correspond to the likely location of these arteries and estimate the distance between those locations using a tape measure. While many applications of the wearable sensing implementations described herein may begin in a clinic or research facility where these direct measurements are appropriate, it is also envisioned that a person's ATD may be estimated outside such facilities.

In one implementation, a camera-based system is employed to estimate a person's ATD using images of the person. In one version, these images include both color images and depth images. In addition, in one version the person whose ATD is being estimated stands in front of the camera system and poses—for example standing with arms outstretched. This allows for a more accurate estimation of the length of a person's arm segments and the width of the person's torso. Conventional methods are employed to estimate the ATD from the captured images. It is noted that image-based ATD estimation is an automated version of the previously-described direct measurement scheme where the person is measured using a tape measure.

In another implementation, a numerical model is generated that estimates ATD based on various prescribed body metrics. In one version, this involves creating a database of direct ATD estimates between the heart and other locations (e.g. the wrist) for multiple individuals (e.g., about 1000). In addition, for each person whose ATD is included in the database, demographic data is collected and added to the database. In one version, this demographic data includes, but is not limited to, various body metrics such as one or more of the person's height, or weight, or waist circumference, or fingertip-to-fingertip span (also known as wingspan), or shoulder width, or torso height (i.e., waist to shoulder), or individual joint lengths, or gender, or race, or age. For convenience, in one version the body metrics chosen to be collected are of the kinds that are readily determinable. These metrics can be collected directly from the person, or if feasible from an existing electronic database. Appropriate conventional methods (e.g., linear regression, support vector machine (SVM) regression, non-linear least squares regression, classification and regression trees (CARTs)) are then employed to learn a numerical model that correlates the aforementioned body metrics to an ATD between a person's heart and various other arterial locations on the body.

Once the numerical model is available, the aforementioned body metrics for a new person (whose ATDs where not directly measured) are collected and the model is used to generate an estimate the new person's ATD between his or her heart and an arterial location of interest. This assumes of course that the arterial location of interest is one of the locations that were used to generate the ATD model.

In yet another implementation, the foregoing ATD model is generated not only using the aforementioned body metrics, but also includes the previously-described image-based ATD estimation as one of the body metrics. It is believed that the addition of image-based ATD estimations will create a more accurate ATD model.

Figure 5:
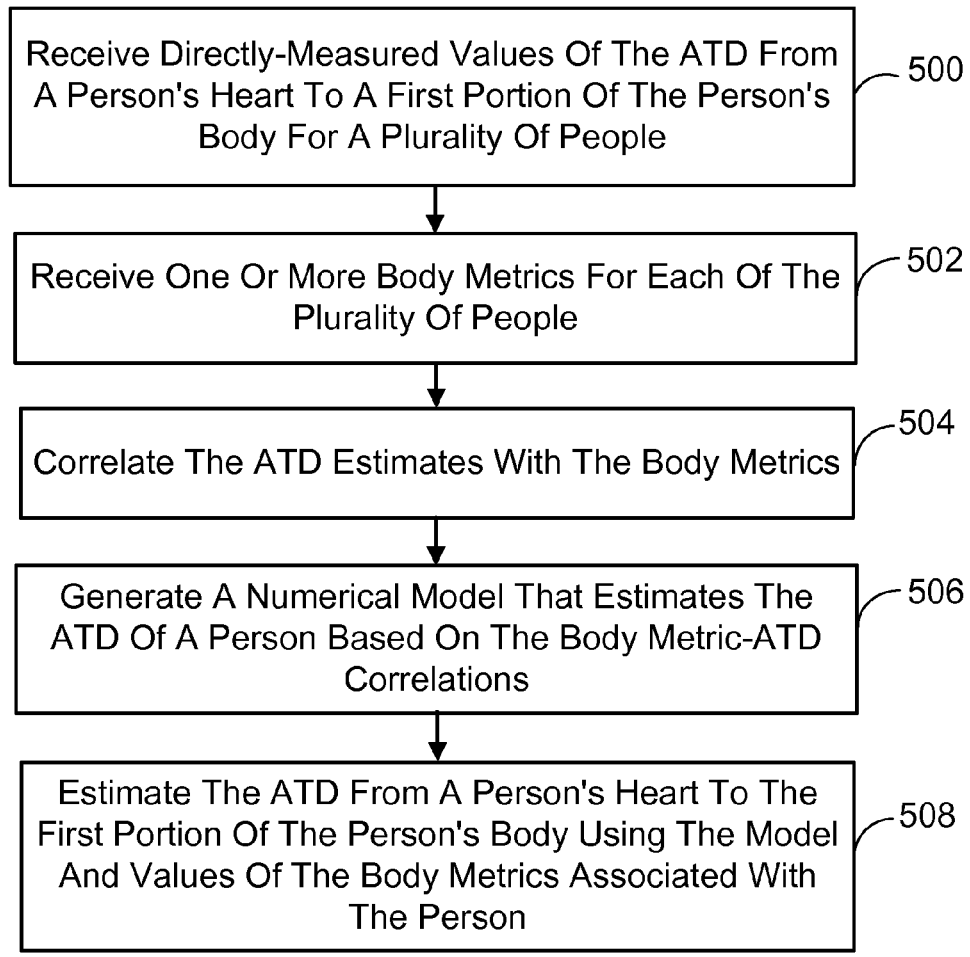
FIG. 5 is a flow diagram illustrating an exemplary embodiment, in simplified form, of a process for estimating the arterial travel distance (ATD) from a user's heart to a portion of the user's body underlying the wearable sensing band.

In view of the foregoing and referring to FIG. 5, in one general implementation, estimating the ATD from a person's heart to a first portion of the person's body, includes using one or more computing devices to perform the following process actions. First, directly-measured values of the ATD from a person's heart to a first portion of the person's body are received for a plurality of people (process action 500). In addition, one or more body metrics for each of the plurality of people are received (process action 502). The ATD estimates are then correlated with the body metrics (process action 504), and a numerical model is generated that estimates the ATD of a person based on the body metric-ATD correlations (process action 506). Once the ATD numerical model is available, the ATD from a person's heart to the first portion of the person's body is estimated using the model and values of the body metrics associated with the person (process action 508).

2.0 Exemplary Operating Environments

Figure 6:
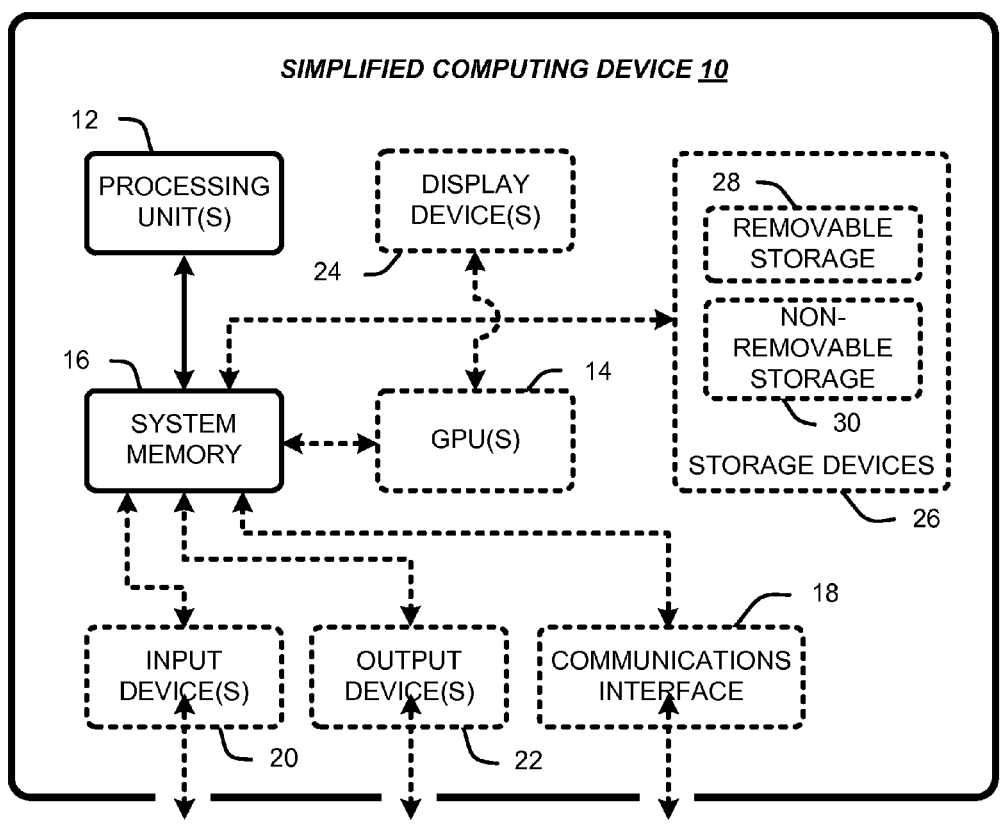
FIG. 6 is a diagram depicting a general purpose computing device constituting an exemplary system for implementing wearable sensing implementations described herein.

The wearable sensing implementations described herein are operational within numerous types of general purpose or special purpose computing system environments or configurations. FIG. 6 illustrates a simplified example of a general-purpose computer system on which various implementations and elements of wearable sensing, as described herein, may be implemented. It is noted that any boxes that are represented by broken or dashed lines in the simplified computing device 10 shown in FIG. 6 represent alternate implementations of the simplified computing device. As described below, any or all of these alternate implementations may be used in combination with other alternate implementations that are described throughout this document. The simplified computing device 10 is typically found in devices having at least some minimum computational capability such as personal computers (PCs), server computers, handheld computing devices, laptop or mobile computers, communications devices such as cell phones and personal digital assistants (PDAs), multiprocessor systems, microprocessor-based systems, set top boxes, programmable consumer electronics, network PCs, minicomputers, mainframe computers, and audio or video media players.

To allow a device to realize the wearable sensing implementations described herein, the device should have a sufficient computational capability and system memory to enable basic computational operations. In particular, the computational capability of the simplified computing device 10 shown in FIG. 6 is generally illustrated by one or more processing unit(s) 12, and may also include one or more graphics processing units (GPUs) 14, either or both in communication with system memory 16. Note that that the processing unit(s) 12 of the simplified computing device 10 may be specialized microprocessors (such as a digital signal processor (DSP), a very long instruction word (VLIW) processor, a field-programmable gate array (FPGA), or other micro-controller) or can be conventional central processing units (CPUs) having one or more processing cores.

In addition, the simplified computing device 10 may also include other components, such as, for example, a communications interface 18. The simplified computing device 10 may also include one or more conventional computer input devices 20 (e.g., touchscreens, touch-sensitive surfaces, pointing devices, keyboards, audio input devices, voice or speech-based input and control devices, video input devices, haptic input devices, devices for receiving wired or wireless data transmissions, and the like) or any combination of such devices.

Similarly, various interactions with the simplified computing device 10 and with any other component or feature of wearable sensing, including input, output, control, feedback, and response to one or more users or other devices or systems associated with wearable sensing, are enabled by a variety of Natural User Interface (NUI) scenarios. The NUI techniques and scenarios enabled by wearable sensing include, but are not limited to, interface technologies that allow one or more users user to interact with wearable sensing in a "natural" manner, free from artificial constraints imposed by input devices such as mice, keyboards, remote controls, and the like.

Such NUI implementations are enabled by the use of various techniques including, but not limited to, using NUI information derived from user speech or vocalizations captured via microphones or other sensors. Such NUI implementations are also enabled by the use of various techniques including, but not limited to, information derived from a user's facial expressions and from the positions, motions, or orientations of a user's hands, fingers, wrists, arms, legs, body, head, eyes, and the like, where such information may be captured using various types of 2D or depth imaging devices such as stereoscopic or time-of-flight camera systems, infrared camera systems, RGB (red, green and blue) camera systems, and the like, or any combination of such devices. Further examples of such NUI implementations include, but are not limited to, NUI information derived from touch and stylus recognition, gesture recognition (both onscreen and adjacent to the screen or display surface), air or contact-based gestures, user touch (on various surfaces, objects or other users), hover-based inputs or actions, and the like. Such NUI implementations may also include, but are not limited, the use of various predictive machine intelligence processes that evaluate current or past user behaviors, inputs, actions, etc., either alone or in combination with other NUI information, to predict information such as user intentions, desires, and/or goals. Regardless of the type or source of the NUI-based information, such information may then be used to initiate, terminate, or otherwise control or interact with one or more inputs, outputs, actions, or functional features of wearable sensing.

However, it should be understood that the aforementioned exemplary NUI scenarios may be further augmented by combining the use of artificial constraints or additional signals with any combination of NUI inputs. Such artificial constraints or additional signals may be imposed or generated by input devices such as mice, keyboards, and remote controls, or by a variety of remote or user worn devices such as accelerometers, electromyography (EMG) sensors for receiving myoelectric signals representative of electrical signals generated by user's muscles, heart-rate monitors, galvanic skin conduction sensors for measuring user perspiration, wearable or remote biosensors for measuring or otherwise sensing user brain activity or electric fields, wearable or remote biosensors for measuring user body temperature changes or differentials, and the like. Any such information derived from these types of artificial constraints or additional signals may be combined with any one or more NUI inputs to initiate, terminate, or otherwise control or interact with one or more inputs, outputs, actions, or functional features of wearable sensing.

The simplified computing device 10 may also include other optional components such as one or more conventional computer output devices 22 (e.g., display device(s) 24, audio output devices, video output devices, devices for transmitting wired or wireless data transmissions, and the like). Note that typical communications interfaces 18, input devices 20, output devices 22, and storage devices 26 for general-purpose computers are well known to those skilled in the art, and will not be described in detail herein.

The simplified computing device 10 shown in FIG. 6 may also include a variety of computer-readable media. Computer-readable media can be any available media that can be accessed by the computer 10 via storage devices 26, and can include both volatile and nonvolatile media that is either removable 28 and/or non-removable 30, for storage of information such as computer-readable or computer-executable instructions, data structures, program modules, or other data. Computer-readable media includes computer storage media and communication media. Computer storage media refers to tangible computer-readable or machine-readable media or storage devices such as digital versatile disks (DVDs), blu-ray discs (BD), compact discs (CDs), floppy disks, tape drives, hard drives, optical drives, solid state memory devices, random access memory (RAM), read-only memory (ROM), electrically erasable programmable read-only memory (EEPROM), CD-ROM or other optical disk storage, smart cards, flash memory (e.g., card, stick, and key drive), magnetic cassettes, magnetic tapes, magnetic disk storage, magnetic strips, or other magnetic storage devices. Further, a propagated signal is not included within the scope of computer-readable storage media.

Retention of information such as computer-readable or computer-executable instructions, data structures, program modules, and the like, can also be accomplished by using any of a variety of the aforementioned communication media (as opposed to computer storage media) to encode one or more modulated data signals or carrier waves, or other transport mechanisms or communications protocols, and can include any wired or wireless information delivery mechanism. Note that the terms "modulated data signal" or "carrier wave" generally refer to a signal that has one or more of its characteristics set or changed in such a manner as to encode information in the signal. For example, communication media can include wired media such as a wired network or direct-wired connection carrying one or more modulated data signals, and wireless media such as acoustic, radio frequency (RF), infrared, laser, and other wireless media for transmitting and/or receiving one or more modulated data signals or carrier waves.

Furthermore, software, programs, and/or computer program products embodying some or all of the various wearable sensing implementations described herein, or portions thereof, may be stored, received, transmitted, or read from any desired combination of computer-readable or machine-readable media or storage devices and communication media in the form of computer-executable instructions or other data structures. Additionally, the claimed subject matter may be implemented as a method, apparatus, or article of manufacture using standard programming and/or engineering techniques to produce software, firmware, hardware, or any combination thereof to control a computer to implement the disclosed subject matter. The term "article of manufacture" as used herein is intended to encompass a computer program accessible from any computer-readable device, or media.

The wearable sensing implementations described herein may be further described in the general context of computer-executable instructions, such as program modules, being executed by a computing device. Generally, program modules include routines, programs, objects, components, data structures, and the like, that perform particular tasks or implement particular abstract data types. The wearable sensing implementations may also be practiced in distributed computing environments where tasks are performed by one or more remote processing devices, or within a cloud of one or more devices, that are linked through one or more communications networks. In a distributed computing environment, program modules may be located in both local and remote computer storage media including media storage devices. Additionally, the aforementioned instructions may be implemented, in part or in whole, as hardware logic circuits, which may or may not include a processor.

Alternatively, or in addition, the functionality described herein can be performed, at least in part, by one or more hardware logic components. For example, and without limitation, illustrative types of hardware logic components that can be used include field-programmable gate arrays (FPGAs), application-specific integrated circuits (ASICs), application-specific standard products (ASSPs), system-on-a-chip systems (SOCs), complex programmable logic devices (CPLDs), and so on.

3.0 Other Implementations

It is noted that any or all of the aforementioned implementations throughout the description may be used in any combination desired to form additional hybrid implementations. In addition, although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What has been described above includes example implementations. It is, of course, not possible to describe every conceivable combination of components or methodologies for purposes of describing the claimed subject matter, but one of ordinary skill in the art may recognize that many further combinations and permutations are possible. Accordingly, the claimed subject matter is intended to embrace all such alterations, modifications, and variations that fall within the spirit and scope of the appended claims.

In regard to the various functions performed by the above described components, devices, circuits, systems and the like, the terms (including a reference to a "means") used to describe such components are intended to correspond, unless otherwise indicated, to any component which performs the specified function of the described component (e.g., a functional equivalent), even though not structurally equivalent to the disclosed structure, which performs the function in the herein illustrated exemplary aspects of the claimed subject matter. In this regard, it will also be recognized that the foregoing implementations include a system as well as a computer-readable storage media having computer-executable instructions for performing the acts and/or events of the various methods of the claimed subject matter.

There are multiple ways of realizing the foregoing implementations (such as an appropriate application programming interface (API), tool kit, driver code, operating system, control, standalone or downloadable software object, or the like), which enable applications and services to use the implementations described herein. The claimed subject matter contemplates this use from the standpoint of an API (or other software object), as well as from the standpoint of a software or hardware object that operates according to the implementations set forth herein. Thus, various implementations described herein may have aspects that are wholly in hardware, or partly in hardware and partly in software, or wholly in software.

The aforementioned systems have been described with respect to interaction between several components. It will be appreciated that such systems and components can include those components or specified sub-components, some of the specified components or sub-components, and/or additional components, and according to various permutations and combinations of the foregoing. Sub-components can also be implemented as components communicatively coupled to other components rather than included within parent components (e.g., hierarchical components).

Additionally, it is noted that one or more components may be combined into a single component providing aggregate functionality or divided into several separate sub-components, and any one or more middle layers, such as a management layer, may be provided to communicatively couple to such sub-components in order to provide integrated functionality. Any components described herein may also interact with one or more other components not specifically described herein but generally known by those of skill in the art.

4.0 Claim Support and Further Implementations

The following paragraphs summarize various examples of implementations which may be claimed in the present document. However, it should be understood that the implementations summarized below are not intended to limit the subject matter which may be claimed in view of the foregoing descriptions. Further, any or all of the implementations summarized below may be claimed in any desired combination with some or all of the implementations described throughout the foregoing description and any implementations illustrated in one or more of the figures, and any other implementations described below. In addition, it should be noted that the following implementations are intended to be understood in view of the foregoing description and figures described throughout this document.

In one implementation, a wearable sensing band includes a strap that is attached to a first portion of the user's body; one or more primary electrocardiography (ECG) electrodes disposed on the strap such that whenever the wearable sensing band is worn by the user, the primary ECG electrodes are in electrical contact with the first portion of the user's body; one or more secondary ECG electrodes disposed on the strap such that whenever the wearable sensing band is worn by the user, the secondary ECG electrodes are electrically isolated from the first portion of the user's body and are positioned so as to be contacted by a second portion of the user's body located on the opposite side of the user's heart from the first portion of the user's body; and one or more pulse pressure wave arrival (PPWA) sensors disposed on the strap such that whenever the wearable sensing band is worn by the user, the PPWA sensors are in proximity to or contacting the first portion of the user's body. The aforementioned primary and secondary ECG electrodes detect an ECG signal whenever the secondary ECG electrodes make electrical contact with the second portion of the user's body, and the PPWA sensors sense an arrival of a pulse pressure wave to the first portion of the user's body from the user's heart.

In one implementation, the first portion of the user's body is a place on a person's body where movement in an underlying artery can be sensed, and where the strap can be either wrapped around and tightened or the strap can be adhered to. More particularly, the first portion of the user's body can be one of a wrist, or a forearm, or an upper arm, or torso, or an upper leg, or a lower leg, or an ankle.

In one implementation, there are multiple primary ECG electrodes which are electrically connected to each other; or there are multiple secondary ECG electrodes which are electrically connected to each other; or there are multiple primary ECG electrodes which are electrically connected to each other, and multiple secondary ECG electrodes which are electrically connected to each other. In another implementation, there are multiple primary ECG electrodes which are electrically isolated from each other; or there are multiple secondary ECG electrodes which are electrically isolated from each other; or there are multiple primary ECG electrodes which are electrically isolated from each other, and multiple secondary ECG electrodes which are electrically isolated from each other. Further, in one implementation, at least one of the one or more secondary ECG electrodes is of a type that established electrical contact with the second portion of the user's body through clothing. Still further, in one implementation, where the first portion of the user's body is the user's wrist, the one or more primary ECG electrodes are disposed on a part of the strap touching the underside of the user's wrist. Yet further, in one implementation, the one or more primary ECG electrodes are disposed on a first side of the strap, and the one or more secondary ECG electrodes are disposed on the opposite side of the strap.

In one implementation, at least one of the one or more pulse pressure wave arrival (PPWA) sensors is an optical sensor. In another implementation, at least one of the one or more pulse pressure wave arrival (PPWA) sensors is a pressure sensor. Further, in one implementation, where the first portion of the user's body is the user's wrist, the one or more pulse pressure wave arrival (PPWA) sensors are disposed on a part of the strap touching the underside of the user's wrist.

The implementations and versions described in any of the previous paragraphs in this section may also be combined with each other, and with one or more of the implementations and versions described prior to this section. For example, some or all of the preceding implementations and versions may be combined with the foregoing implementation where the first portion of the user's body is the user's wrist, the one or more pulse pressure wave arrival (PPWA) sensors are disposed on a part of the strap touching the underside of the user's wrist. In addition, some or all of the preceding implementations and versions may be combined with the foregoing implementation where the one or more primary ECG electrodes are disposed on a first side of the strap, and the one or more secondary ECG electrodes are disposed on the opposite side of the strap.

In one implementation, a wearable sensing band is part of a system for computing at least one of a pulse transit time (PTT) or a pulse wave velocity (PWV) of a user. This system includes, in addition to the above-described wearable sensing band, a computing device which executes program modules of a computer program. The computing device is directed by the program modules of the computer program to estimate the time a pulse pressure wave leaves the user's heart using the ECG signal, and establish the time the pulse pressure wave arrives at the first portion of the user's body using the sensed arrival of the pulse pressure wave.

In one implementation, the computing device is further directed by the program modules of the computer program to compute the pulse transit time (PTT) of a pulse pressure wave traveling through the user's arteries from the user's heart to the first portion of the user's body by subtracting the time the pulse pressure wave left the user's heart from the arrival time of the pulse pressure wave to the first portion of the user's body. In a version of this implementation, the computing device is further directed by the program modules of the computer program to obtain an estimate of the arterial travel distance (ATD) between the user's heart and the first portion of the user's body, and compute a pulse wave velocity (PWV) using the PTT and ATD estimate. In one implementation, the abovementioned program module for obtaining an estimate of the ATD between the user's heart and the first portion of the user's body, includes using images of the user to estimate the user's ATD.

In one implementation, the system also includes a communication component for transmitting data representative of at least one of the computed PTT or PWV of the user via a computer network. In this implementation, the computing device is further directed by the program modules of the computer program to transmit the representative data to one or more remote computing devices.

In another implementation, the system includes a communication component for transmitting data representative of the time the pulse pressure wave left the user's heart and the arrival time of the pulse pressure wave arrived at the first portion of the user's body via a computer network. In this implementation, the computing device is further directed by the program modules of the computer program to transmit the representative data to one or more remote computing devices for computation of at least one of the PTT or PWV of the user based on the transmitted representative data.

As indicated previously, the implementations and versions described in any of the previous paragraphs in this section may also be combined with each other, and with one or more of the implementations and versions described prior to this section. For example, some or all of the preceding implementations and versions may be combined with the foregoing implementation where the system includes a communication component for transmitting data representative of at least one of the computed PTT or PWV of the user via a computer network; and wherein the processor is further configured to transmit the representative data to one or more remote computing devices. In addition, some or all of the preceding implementations and versions may be combined with the foregoing implementation where the system includes a communication component for transmitting data representative of the time the pulse pressure wave left the user's heart and the arrival time of the pulse pressure wave arrived at said first portion of the user's body via a computer network; and wherein the processor is further configured to transmit said representative data to one or more remote computing devices for computation of at least one of the PTT or PWV of the user based on the transmitted representative data.

In one implementation, a computer-implemented process is employed for estimating the arterial travel distance (ATD) from a person's heart to a first portion of the person's body. This process uses one or more computing devices to perform the following process actions, which whenever plural computing devices are used are in communication with each other via a computer network. More particularly, the process involves receiving directly-measured values of the ATD from a person's heart to a first portion of the person's body for a plurality of people; receiving one or more body metrics for each of the plurality of people; correlating the ATD estimates with the body metrics; generating a numerical model that estimates the ATD from a person's heart to a first portion of the person's body based on the body metric-ATD correlations; and estimating the ATD from a person's heart to the first portion of the person's body using the numerical model and values of the body metrics associated with the person.

It is noted that in one version, the body metrics include at least one of the person's height, or weight, or waist circumference, or fingertip-to-fingertip span, or shoulder width, or torso height, or individual joint lengths, or gender, or race, or age. In addition to at least one of the foregoing body metrics, in one version, the body metrics include an estimate of the person's ATD derived from images of the user.

In various implementations, a wearable sensing band system is implemented by means for computing at least one of a pulse transit time (PTT) or a pulse wave velocity (PWV) of a user.

For example, in one implementation, a wearable sensing band system includes a strap means for attaching the wearable sensing band to a first portion of the user's body; one or more primary electrocardiography (ECG) electrode means disposed on the strap means for making electrical contact with the first portion of the user's body whenever the wearable sensing band is worn by the user; one or more secondary ECG electrode means disposed on the strap for making electrical contact with a second portion of the user's body located on the opposite side of the user's heart from the first portion of the user's body; and one or more pulse pressure wave arrival (PPWA) sensors means disposed on the strap in proximity to or contacting the first portion of the user's body for sensing an arrival of a pulse pressure wave to the first portion of the user's body from the user's heart when the wearable sensing band is worn by the user. The aforementioned primary and secondary ECG electrodes means can detect an ECG signal whenever the secondary ECG electrodes make electrical contact with the second portion of the user's body. In a further implementation, the wearable sensing band also includes a computing device comprising a processor configured to execute an estimating step for estimating the time a pulse pressure wave leaves the user's heart using the ECG signal, and an establishing step for establishing the time said pulse pressure wave arrives at said first portion of the user's body using the sensed arrival of the pulse pressure wave.

In various implementations, an arterial travel distance (ATD) estimating process is implemented by a step for estimating the arterial travel distance (ATD) from a person's heart to a first portion of the person's body.

For example, in one implementation, the arterial travel distance (ATD) estimating process includes a step for using one or more computing devices to perform the following process actions, which whenever plural computing devices are used are in communication with each other via a computer network: a step for receiving directly-measured values of the ATD from a person's heart to a first portion of the person's body for a plurality of people; a step for receiving one or more body metrics for each of the plurality of people; a step for correlating the ATD estimates with the body metrics; a step for generating a numerical model that estimates the ATD from a person's heart to a first portion of the person's body based on the body metric-ATD correlations; and a step for estimating the ATD from a person's heart to said first portion of the person's body using the numerical model and values of said body metrics associated with the person.

Wherefore, what is claimed is:

1. A computer-implemented process for estimating the arterial travel distance (ATD) from a person's heart to a first portion of the person's body, comprising the actions of:
   using one or more computing devices to perform the following process actions, which whenever plural computing devices are used are in communication with each other via a computer network:
   receiving directly-measured values of the ATD from a person's heart to a first portion of the person's body for a plurality of people;
   receiving one or more body metrics for each of the plurality of people;
   correlating the ATD estimates with the body metrics;
   generating a numerical model that estimates the ATD from a person's heart to a first portion of the person's body based on the body metric-ATD correlations; and
   estimating the ATD from a person's heart to said first portion of the person's body using the numerical model and values of said body metrics associated with the person.

2. The process of claim 1, wherein the body metrics comprises at least one of the person's height, or weight, or waist circumference, or fingertip-to-fingertip span, or shoulder width, or torso height, or individual joint lengths, or gender, or race, or age.

3. The process of claim 2, wherein the body metrics further comprise an estimate of the person's ATD derived from images of the user.

4. A system for estimating the arterial travel distance (ATD) from a person's heart to a first portion of the person's body, comprising:
   one or more computing devices, said computing devices being in communication with each other whenever there is a plurality of computing devices; and
   an ATD estimating computer program having a plurality of sub-programs executable by the one or more computing devices, the one or more computing devices being directed by the sub-programs of the computer program to,
      receive directly-measured values of the ATD from a person's heart to a first portion of the person's body for a plurality of people,
      receive one or more body metrics for each of the plurality of people,
      correlate the ATD estimates with the body metrics, and
      generate a numerical model that estimates the ATD from a person's heart to a first portion of the person's body based on the body metric-ATD correlations.

5. The system of claim 4, wherein the body metrics comprises at least one of the person's height, or weight, or waist circumference, or fingertip-to-fingertip span, or shoulder width, or torso height, or individual joint lengths, or gender, or race, or age.

6. The system of claim 5, wherein the body metrics further comprise an estimate of the person's ATD derived from images of the user.

7. A system for computing a pulse wave velocity (PWV) of a user, comprising:
   a wearable sensing band comprising,
      a strap which is attached to a first portion of the user's body,
      one or more primary electrocardiography (ECG) electrodes disposed on the strap such that whenever the wearable sensing band is worn by the user, the primary ECG electrodes are in electrical contact with said first portion of the user's body,
      one or more secondary ECG electrodes disposed on the strap such that whenever the wearable sensing band is worn by the user, the secondary ECG electrodes are electrically isolated from said first portion of the user's body and are positioned so as to be contacted by a second portion of the user's body located on the opposite side of the user's heart from said first portion of the user's body,
      one or more pulse pressure wave arrival (PPWA) sensors disposed on the strap such that whenever the wearable sensing band is worn by the user, the PPWA sensors are in proximity to or contacting said first portion of the user's body, wherein
      said primary and secondary ECG electrodes detect an ECG signal whenever the secondary ECG electrodes make electrical contact with said second portion of the user's body, and said PPWA sensors sense an arrival of a pulse pressure wave to said first portion of the user's body from the user's heart, and
   a computing device which executes program modules of a computer program, the computing device being directed by the program modules of the computer program to,
      estimate the time a pulse pressure wave leaves the user's heart using the ECG signal,
      establish the time said pulse pressure wave arrives at said first portion of the user's body using the sensed arrival of the pulse pressure wave,
      compute the pulse transit time (PTT) of a pulse pressure wave traveling through the user's arteries from the user's heart to said first portion of the user's body by subtracting the time the pulse pressure wave left the user's heart from the arrival time of the pulse pressure wave to said first portion of the user's body,
      obtain an estimate of the arterial travel distance (ATD) between the user's heart and said first portion of the user's body using a numerical model and values of prescribed body metrics associated with the user, wherein the numerical model estimates the ATD from a person's heart to a first portion of the user's body based on body metric-ATD correlations, and
      compute the pulse wave velocity (PWV) using the PTT and ATD estimate.

8. The system of claim 7, wherein the wearable sensing band further comprises:
   a communication component for transmitting data representative of the computed PTT and the prescribed body metrics associated with the user, via a computer network; and wherein the computing device is further directed by the program modules of the computer program to, transmit said representative data to one or more remote computing devices for computation of the ATD for the user based on the transmitted representative data, and receive the estimated ATD for the user that was computed by the one or more remote computing devices.

9. The system of claim 8, wherein the one or more remote computing devices computes the ATD estimate for the user by generating said numerical model that estimates the ATD from a user's heart to a first portion of the user's body based on the body metric-ATD correlations.

10. The system of claim 9, wherein the one or more remote computing devices generates said numerical model using an ATD estimating computer program having a plurality of sub-programs executable by the one or more remote computing devices, the one or more remote computing devices being directed by the sub-programs of the computer program to, receive directly-measured values of the ATD from a person's heart to a first portion of the person's body for a plurality of people, receive said prescribed body metrics for each of the plurality of people, correlate the ATD estimates with the body metrics, and generate the numerical model that estimates the ATD from a person's heart to a first portion of the person's body based on the body metric-ATD correlations.

11. The system of claim 10, wherein the prescribed body metrics comprises at least one of the person's height, or weight, or waist circumference, or fingertip-to-fingertip span, or shoulder width, or torso height, or individual joint lengths, or gender, or race, or age.

12. The system of claim 11, wherein the prescribed body metrics further comprise an estimate of the person's ATD derived from images of the user.

\* \* \* \* \*